United States Patent [19]
Caracciolo

[11] Patent Number: 5,725,593
[45] Date of Patent: Mar. 10, 1998

[54] TOTAL ANATOMIC HIP PROSTHESIS

[76] Inventor: Francesco Caracciolo, Via Sangallo, 2 - 20133 Milan, Italy

[21] Appl. No.: 739,929

[22] Filed: Oct. 30, 1996

Related U.S. Application Data

[63] Continuation of Ser. No. 531,349, Sep. 20, 1995, abandoned.

[30] Foreign Application Priority Data

Feb. 22, 1995 [IT] Italy ................... MI95A0322

[51] Int. Cl.⁶ ................... A61F 2/34; A61F 2/36
[52] U.S. Cl. ................... 623/22; 623/23
[58] Field of Search ................... 623/18, 22, 23; 606/65, 70

[56] References Cited

U.S. PATENT DOCUMENTS

| | | | |
|---|---|---|---|
| 3,521,302 | 7/1970 | Muller | 623/22 |
| 3,554,193 | 1/1971 | Konstantinov | 606/65 |
| 4,650,491 | 3/1987 | Parchinski | 623/22 |
| 4,871,368 | 10/1989 | Wagner | 623/22 |
| 5,057,111 | 10/1991 | Park | 606/72 |
| 5,092,898 | 3/1992 | Bekki et al. | 623/22 |
| 5,358,532 | 10/1994 | Evans et al. | 623/22 |

FOREIGN PATENT DOCUMENTS

| | | | |
|---|---|---|---|
| 0626249 | 11/1981 | Switzerland | 623/22 |
| 2033755 | 5/1980 | United Kingdom | 623/23 |

Primary Examiner—John G. Weiss
Assistant Examiner—Bruce E. Snow
Attorney, Agent, or Firm—Abelman, Frayne & Schwab

[57] ABSTRACT

It is described a total anatomic hip prosthesis including a hemispherical prosthetic acetabulum standing above a hemispherical cap, both provided with anchorage means fitting by pressure the acetabulum in the iliac fossa and, respectively, the cap on femoral head, said cap being linked to the components that hold it permanently on said femoral head.

15 Claims, 4 Drawing Sheets

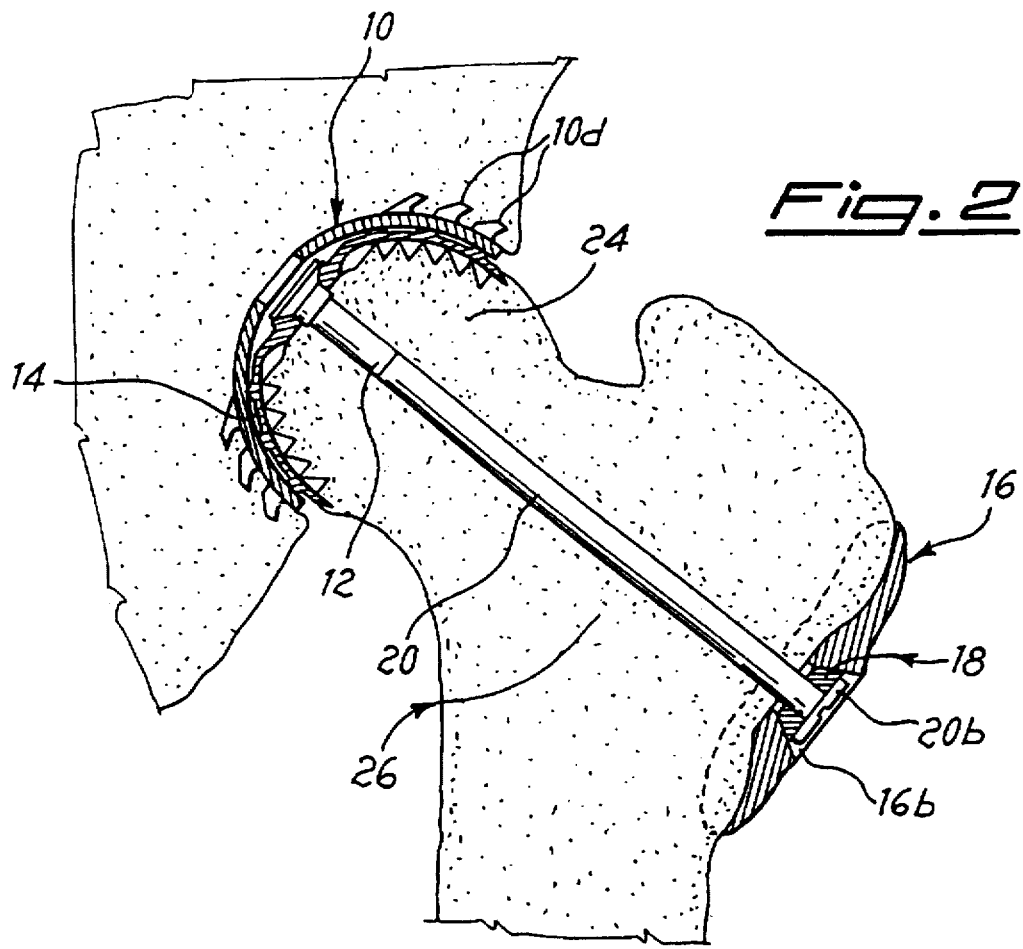
Fig.2
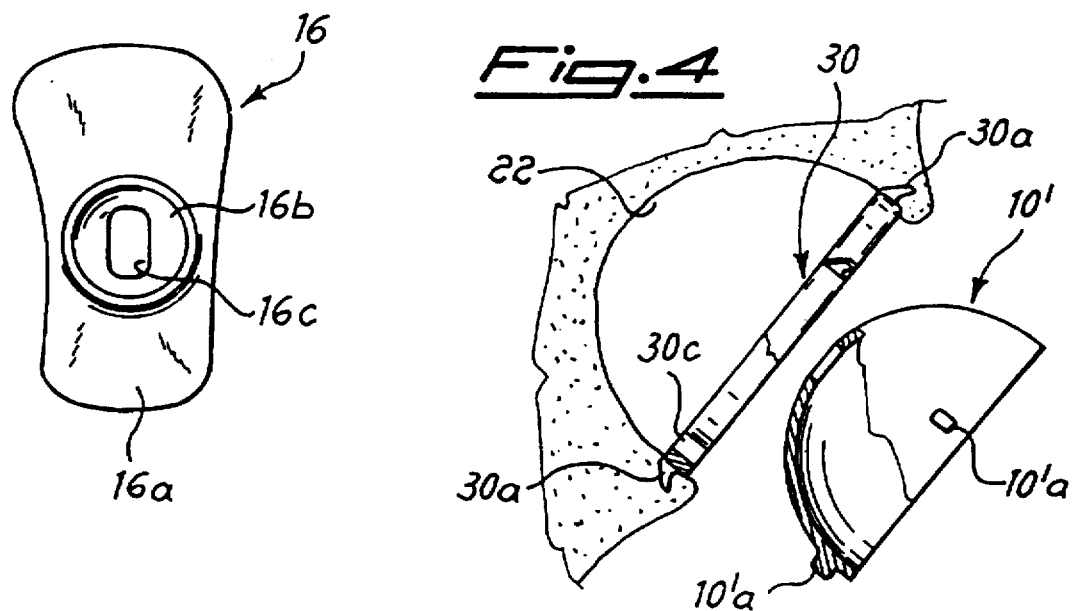
Fig.3
Fig.4

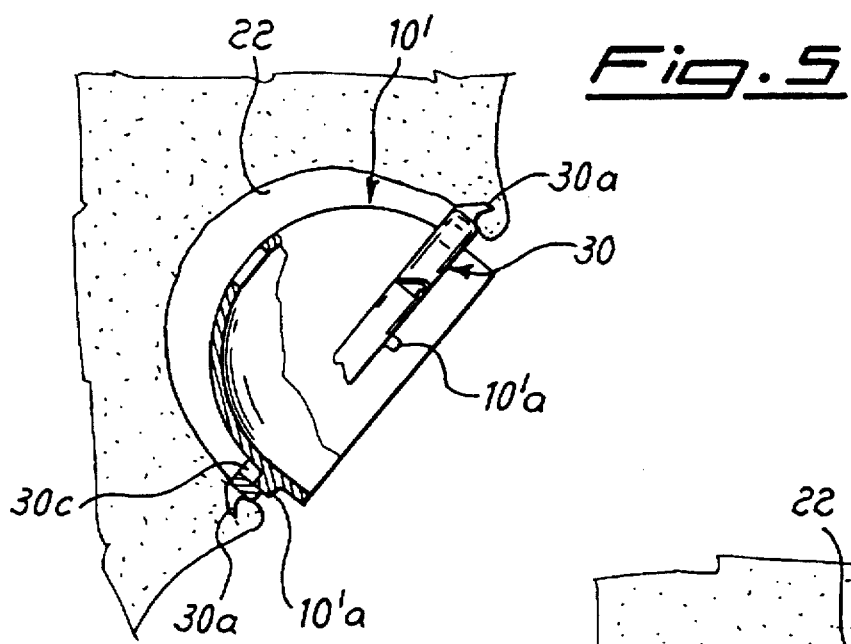
_Fig.5_
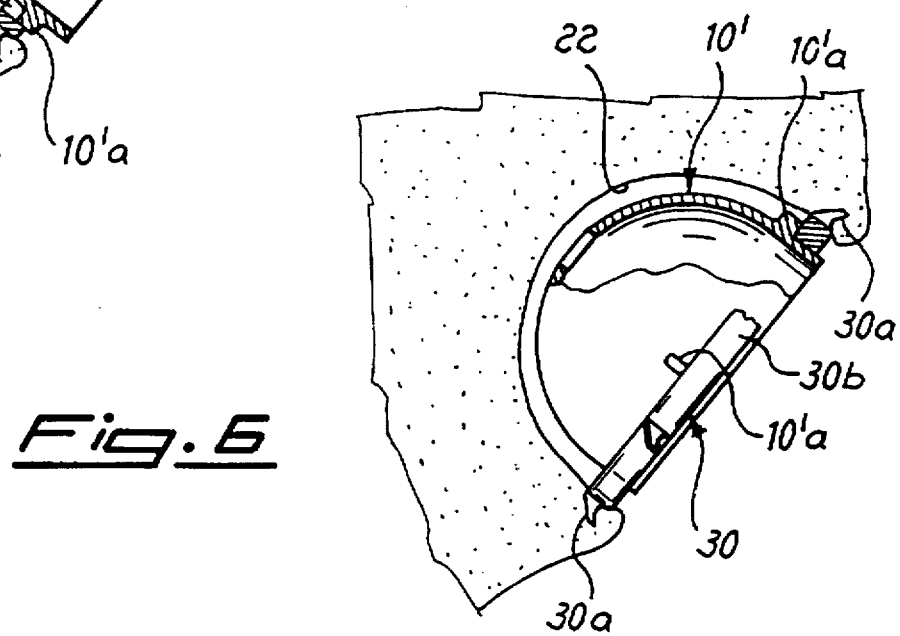
_Fig.6_
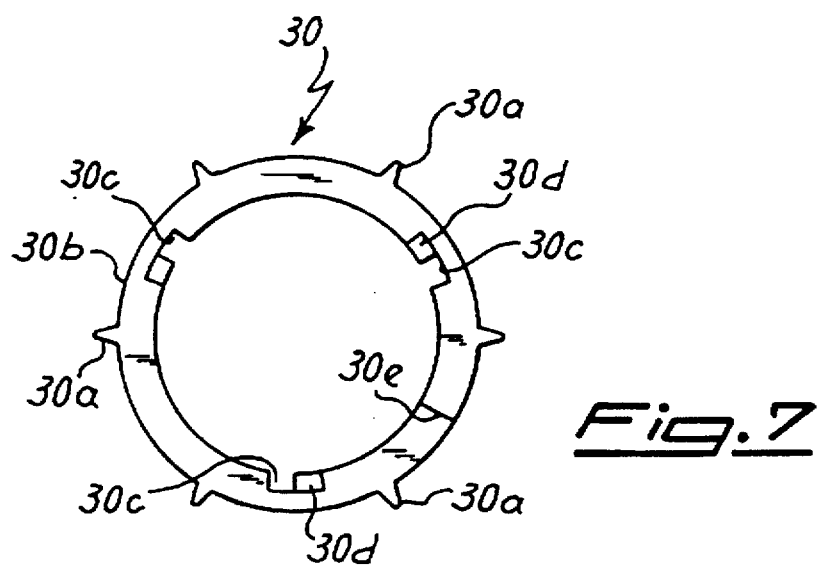
_Fig.7_

TOTAL ANATOMIC HIP PROSTHESIS

This application is a Continuation application under 37 C.F.R. 1.62 of prior application Ser. No. 08/531,349, filed on Sep. 20, 1995, now abandoned.

BACKGROUND OF THE DESCRIPTION

The present invention concerns a total artatomic hip prosthesis with a pressure fitting system to use for the rehabilitation of persons who have not invasive pathologies which require the hip head removal. Said prosthesis is anatomic because it can restore, without relevant alterations, the natural and functional features of the hip. In general terms, the present implantology coxofemoral method is based on an exclusive physical principle, namely that of the "lever", in contrast with natural laws ruling the human physiologic procedure. Some changes have been introduced into the present prosthetic elements, such as new alloys, ceramic or hydroxyapatite coatings (HA), bio-glasses, porous layers, alveolations, the boxing of acetabular jacket or the introduction of new osteocompatible or osteoconducting substances; however, said changes could not avoid the implant failure. In fact, localized pain, incorrect deambulation, mobility of prosthetic acetabulum and of the shaft fixed in the diaphyseal duct, fragmentation of acrylic cement, perimplantar osteolysis with evident reabsorption of the endostal bone and of the cortical diaphysal bone as well as other implant pathologies are still present. Besides, during the operation, fractures in the region of the little trochanter and of the diaphysial spiral may occur, with the following recourse to wiring.

Therefore, the main cause of failure and of implant pathologies is clearly of mechanical nature, mainly due to morphological and functional features which are unsuitable for use.

Now it is the object of the present invention a total anatomic hip prosthesis provided with morphological and functional features which can avoid the aforesaid obstacles, as well as further problems.

SUMMARY OF THE INVENTION

The total anatomic hip prosthesis according to the present invention is characterized by including a hemispherical acetabulum placed above a hemispherical cap, both provided with anchorage means fitting by pressure the acetabulum in the iliac fossa and, respectively, the cap on femoral head, said cap being linked to the components that hold it permanently on said femoral head.

The means of primary anchorage of acetabulum in the iliac fossa are advantageously composed by s plurality of harpoon-shaped teeth working as stabilizers, which are disposed on the external surface of said acetabulum; furthermore, on the aforesaid external surface there are some knurlings which represent a secondary biological anchorage to the iliac fossa. The means of anchorage of the cap to the femoral head are also advantageously constituted by a notching which is placed on the reference plane of said cap.

According to the present invention, a possible embodiment of the prosthesis is due to the fact that the means of anchorage of the acetabulum in the iliac fossa consists of a stabilizing ring, which can be interrupted, if necessary, and which is provided with hooks on the external circumference, said ring being linked to said acetabulum. Said link actually consists of cavities with an inclined plane present in the inner surface of the ring, allowing the fitting and the passage of radial projections on the external surface of the acetabulum, wherein the rotation of the acetabulum produces the aforesaid link. This and other features, as well as the advantages of the total anatomic hip prosthesis according to the present invention, will be more particularly shown in the following detailed description of a non-limiting embodiment with reference to the enclosed figures.

BRIEF DESCRIPTION OF THE DRAWINGS

FIG. 2 shows on a greater scale the components of FIG. 1, assembled and inserted in the patient's hip;

FIG. 3 shows a front view of the stirring component;

FIG. 4 shows an enlarged and partially cross-sectional view of a variation concerning the prosthesis components which ape insertable in the iliac fossa;

FIG. 5 shows the components of FIG. 4, partially inserted in the iliac fossa;

FIG. 6 shows the components of FIG. 5, totally inserted in the iliac fossa;

FIG. 7 shows a plan view of the component according to the variation of FIG. 4, apt to anchor itself in the iliac fossa;

DETAILED DESCRIPTION OF THE PREFERRED EMBODIMENT

Figure 1:
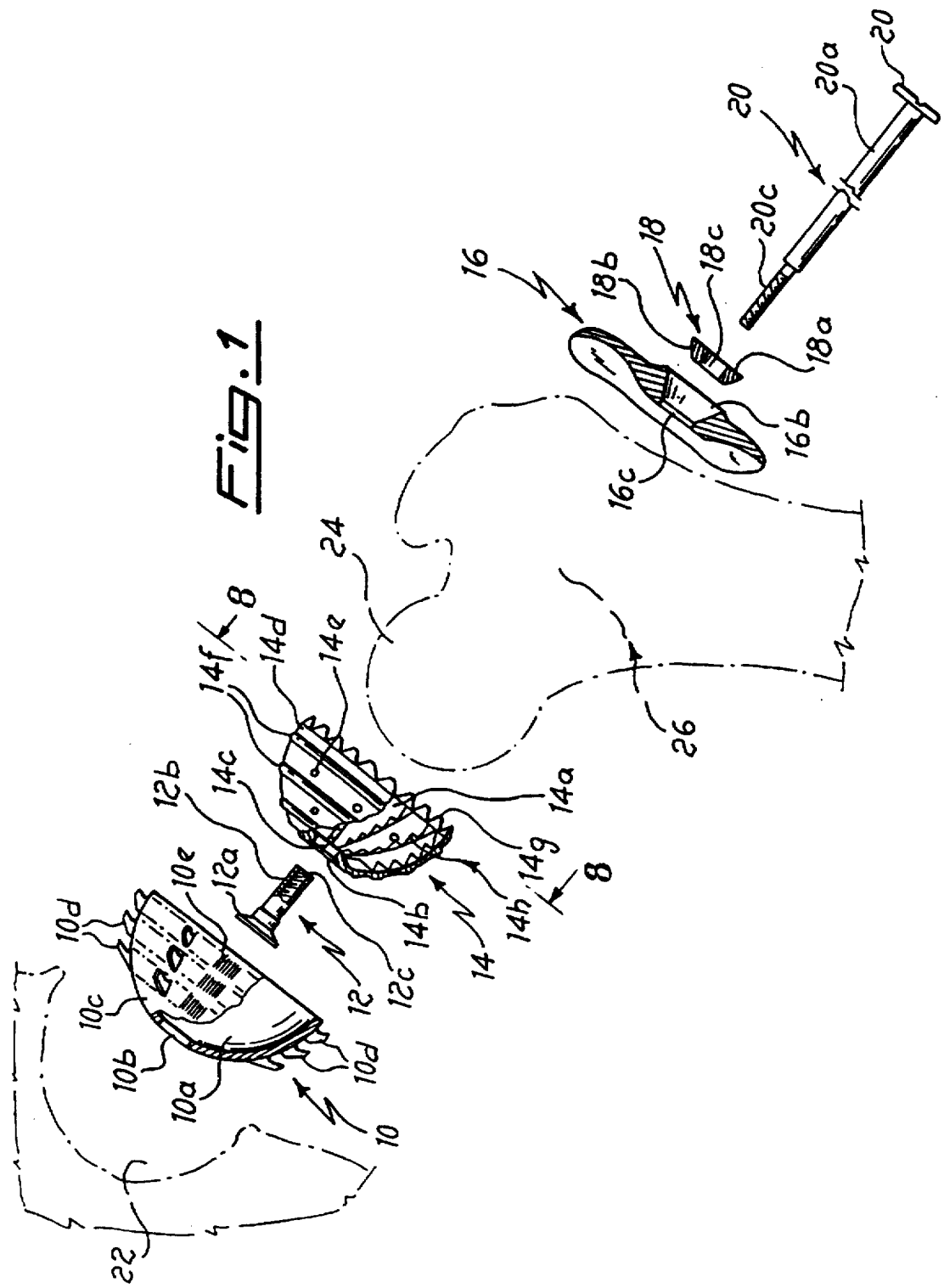
FIG. 1 shows an enlarged and partially cross-sectional view of the components of the total anatomic hip prosthesis according to this invention.

With a reference to FIG. 1 and according to this invention, a preferred embodiment of the total anatomic hip prosthesis is consituted by a plurality of components, such as an acetabulum 10, a higher blind compensator 12, a cap 14, a stirrup 16, a lower passing compensator 18 and a tie 20.

The particular, characterising structure of the aforesaid components is described in the following.

The prosthetic acetabulum 10 has a fundamentally hemispherical structure, hollow inside (10a) and provided on its top with an opening or hole (10b) for technical and biological application purposes. According to a feature of this invention, the acetabulum 10 includes on its external surface (10c) a series of harpoon-shaped teeth (10d), working as stabilizers, as well as some knurlings (10e). A pressure on said teeth (10d) produces a primary anchorage of the acetabulum 10 in the iliac fossa 22 (illustrated by a broken line in FIG. 1), whereas the knurlings (10e) contribute to a better biological fusion between bone and implant.

Now, referring to the higher blind compensator 12, it is structured so as to include a head (12a) and a cylindrical part (12b), internally threaded (12c) for the purpose hereinbelow specified.

The cap 14, which is insertable in the cavity (10a) of the acetabulum 10 (FIG. 1), has a similar hemispherical structure and is hollow inside (14a); on its top there is a seat (14b) with a central opening or hole (14c); this seat (14b) is foreseen to house the head (12a) of the higher blind compensator 12.

The aforesaid cap 14 advantageously has on its external surface (14d) a plurality of holes (14e) as well as circular rises (14f); these latter reduce the friction with the internal cavity (10a) of the acetabulum 10 in order to get the maximum sliding and the minimum dissipation of mechanical power, even with high radial loads, whereas the above mentioned plurality of holes (14e) allows an equitable distribution of the synovial liquid between the two surfaces on sliding phase.

The above circular rises (14f) could be replaced on the external surface (14d) of the cap 14 by radial grains, by segments having a hemisperical or a different shape, by sliding blocks and/or by other mechanical means suitable to the above purposes.

The above mentioned cap 14 includes, also advantageously, a notching (14g) placed on its own reference plane, which contributes to constrain said cap to the femoral head 24 illustrated with a broken line in FIG. 1.

Furthermore, said cap 14 has in its cavity (14a) a particular alveolate structure (14h) apt to guarantee, after the surgical operation for the removal of the pathological tissues, the restoring osteogenesis, the following skeletal and mineral homeostasis as well as the trophism of the underlying bone structure.

The purpose of the cap 14 which replaces the removed pathological tissue is also to satisfy by means of its convexity the static and dynamic and tribological needs, and by means of its concavity to operate in continuous symbiosis with the bone trabecular base.

With regard to the stirrup 16 (FIGS. 1, 2 and 3), it has a structural C-shape which reproduces the shape of the lateral and external cortex of the femur under the great trochanter and includes on its larger surface (16a) a niche (16b) with an oblong and central opening (16c); said niche (16b) is apt to house the lower passing compensator 18 and the head (20b) of the tie 20.

Said lower passing compensator 18 has a flat side (18a) and a convex side (18b) and it is crossed by a hole (18c) for the passage of the tie 20.

As shown in FIG. 2, the tie 20 is positioned in correspondance of the axis of the femoral head and neck 24, which is tilted of about 120°–160° with reference to the gravitational axis: the angle between the axis of the femoral head and neck 24 and the gravitational one (which can vary into a range of about 40°) and, as a consequence, the angle between the axis of the femoral head and neck 24 and the external cortex of the femur under the great trochanter (to which the stirrup 16 is applied) are different from person to person and are therefore specific geometrical characteristics of the femur of each person.

The convex side (18b) of the lower passing compensator 18 [which rotates into the nice (16b) of the stirrup 16] and the central oblong opening (16c) of the niche (16b) of the stirrup 16 allow the tie 20 to rotate (together with the lower passing compensator 18) with reference to the stirrup 16 to modify the angle between the axis of the femoral head and neck 24 and the stirrup 16, adapting the prosthesis to the specific geometrical characteristics of the patient's femur.

Said tie 20 is composed by a cylindrical part (20a), whose end is provided with a head (20b), whereas the other end has a cylindrical threaded part (20c) apt to be screwed in the higher blind compensator 12. According to this invention the application of said prosthesis, used for patients with pathologies requiring the removal of the femoral head 24, implies a simplified process which is summarized hereinafter.

Starting from the resection of the hip joint capsule and from the luxation of the hip, excluding the femoral head 24 and femoral neck osteotomy, the next step is the exposition of the iliac fossa 22. The bore of the iliac fossa 22 is carried out by means of some calibrated osteotribes of increasing diameter, so that the cartilage is completely removed till showing the underlying bone.

Several dimension checks must be carried out before the last osteotribing, which must be carefully executed by hand in order to preserve the edges of the iliac fossa 22.

By boring the iliac cotyloid cavity 22 the dimensions of the selected prosthetic acetabulum 10 must be considered; in fact, the mechanical element 10 for the primary anchorage to the basic bone structure must have a diameter at least 10 mm bigger than the diameter of the last osteotribe which operated on the iliac cotyloid cavity 22.

The acetabulum prosthesis 10 consisting of teeth (10d) and knurlings (10e), in order to favour a prompt biological fusion between bone and implant, in so far as the conditions of interfacial tissue adhering to said prosthesis allow, has to be inserted by pressure in the iliac fossa 22 where it anchors itself.

There is also a second acetabulum prosthesis 10' (FIG. 4) which has a stabilizing ring 30 for the anchorage, wherein said stabilizing ring 30 has to be placed close to the "labrum acetabulare" at the end of the iliac cotyloid cavity 22 borings, as above described.

The stabilizing ring 30 autonomously expands because it includes a junction (30e) and is made of a "shape-memory" material and anchors itself on the position pre-arranged by the operator; it fits in the bone tissues by means of hooks (30a) and alike in order to enable the acetabulum prosthesis 10' to anchor itself to the above mentioned ring 30 by rotation.

Once decided the alignment by means of the suitable "collimator", the concerned bone structure is bored starting from the top of the head 24, then through the centre of the femoral head and, obliquely, through the whole higher epiphysis 26 till reaching the end of the diaphysis under the great trochanter.

The upper half of the femoral head 24 is decorticated by means of a cap toll according to the norms ruling the application of this prosthesis.

Once the decortication is completed, the cap 14 is held to the femoral head 24 through the higher blind compensator 12 [which is threaded inside (12c) and is provided with a head (12a)], the stirrup 16, the lower passing compensator 18 and the tie 20.

Said components (12, 14, 16 and 18) are placed by the following order: the cap 14 is placed on the decorticated head 24, the higher blind compensator 12 is placed in the suitable depression (14b) of the cap 14 and the stirrup 16 with the lower passing compensator 18 is housed under the great trochanter.

The tie 20 is inserted in the lower passing compensator 18 and in said stirrup 16, crosses the higher epiphysis 26 and the femoral head and neck 24 and is screwed to the higher blind compensator 12 placed on the cap 14, assemblying by pressure all the above mentioned components.

With special reference to FIGS. 4, 5, 6 and 7, said Figures show a structural variant of the only components which are insertable in the iliac fossa 22 because the others are similar to the above mentioned ones.

One of the components is constituted by a stabilizing ring 30 of mainly oval section which is provided with hooks (30a) or alike arranged on the external convexity (30b) of said ring 30 which thus may be inserted and linked to the iliac fossa 22 near the "labrum acetabulare".

As hereinafter described, a second component like the prosthetic acetabulum 10' can be linked to the ring 30, wherein said second component has a shape quite similar to the prosthetic acetabulum 10; it lacks teeth (10d) and knurlings (10e) but includes radial projections (10'a) apt to allow the link with said ring 30. For this purpose this latter has some cavities (30c) with inclined planes (30d) which are radially placed in its interior and are as many as the above mentioned radial projections (10'a) of said acetabulum 10'.

The above mentioned link occurs by inserting first the ring 30 in the iliac fossa 22 near the "labrum acetabulare", making sure that the hooks (30a) have a steady setting, then inserting the radial projections (10'a) in the cavities (30c; FIG. 5) until they come out, helped by the inclined planes (30d; FIG. 7); then the acetabulum 10' rotates on its axis till the aforesaid radial projections (10'a) are no longer aligned with said cavities (30c). The stabilizing ring 30 is advantageously made of a "shape-memory" material for application purposes.

Figure 8:
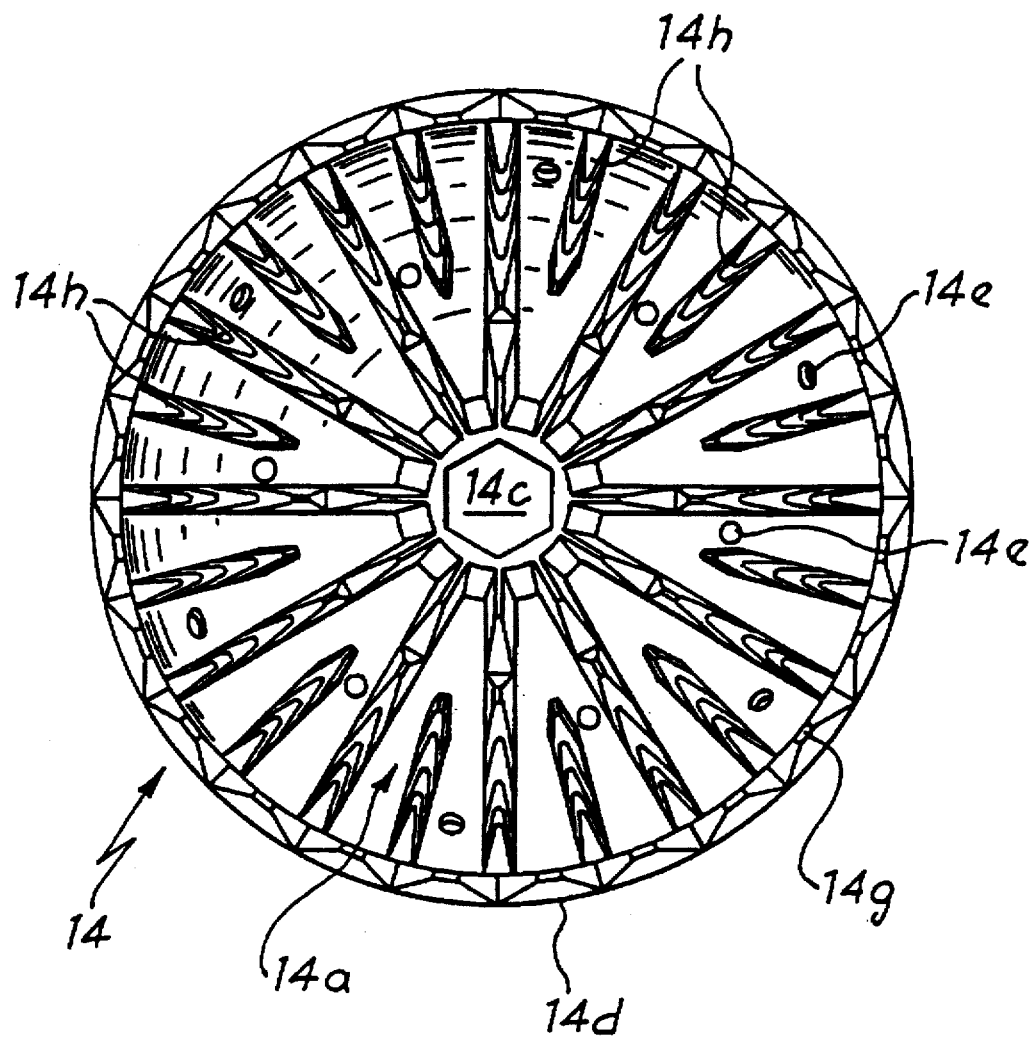
FIG. 8 is a sectional view taken along the line 8—8 of FIG. 1.

With respect to FIG. 8 the alveloate structure 14h comprises a plurality of radial cavities provided with teeth and the notching 14g is realized along the whole rim of the cap 14.

Finally, according to this invention, all total anatomic hip prosthesis components are made of a defined "inert" material and are therefore greatly biocompatible.

From the above said and according to this invention, it is evident that the prosthesis, which was realized thanks to innovatory ideas and with characteristics in accordance with the receiver's needs and physiological structures, as well as with the technological aspects of metallurgy and, above all, with the laws of mechanics in general, with a special regard for statics, dynamics and tribology, intends to solve the following problems:

1) to avoid the occupation of the diaphyseal duct with "power arm" or the rod of the current prostheses, the relevant cementation and all other implant pathological phenomena like this micro- and macromovements which are linked to the morphological and functional features of the mechanical system which was made in accordance with the lever principle;

2) to get a correct balance and an equitable distribution of the statical and dynamical forces which operate on the patient's bone structure;

3) to maintain the sphericity of the iliac cotyloid cavity and to give more stability to the prosthesis acetabulum which with usual prostheses was subjected to oscillatory movements, vibrations and glarings due to the profiles of these hip prostheses which influenced the radially operating forces;

4) to get rid of every type of fitting whose inevitable micro fragmentation, besides annihilating the specific lubricant and dampening function, provokes relevant injuries to the patient's health;

5) to limit the surgical operation to the removal of pathological, soft (fibrous sleeve, ligaments, etc.) and skeletal tissues which constitute the coxofemoral articulation and to safeguard in the concerned anatomic zone the haemopoietic function as well as the skeletal homeostasis and mineral homeostasis (phosphocalcium-metabolism) phenomena;

6) to exclude the use of metals which provoke allergies or electrical or magnetic phenomena causing degenerative illnesses for their toxicity;

7) to share uniformly the radial loads on the surface of adhesion during the relative motion (sliding);

8) to preclude phenomena of dynamic instability;

9) to replace the "double curving" with innovatory and technical contrivances which, because of the reduced direct contact between the operating surfaces, minimize the "sliding friction resistance";

10) to share equitably the available flowing substance (synovial liquid≈3.0 ml) on the surfaces with direct contact and with "limit or epilaminic friction";

11) to get, with great radial loads, a maximum sliding, a minimum dispersion of mechanical power because of friction and large movements in all directions.

Finally, it is clear that modifications on the prosthesis according to the invention can be carried by the skilled in the art without departing from the scope of the following claims.

I claim:

1. Total anatomic hip prosthesis for patients who do not need the femoral head removed, which comprises a hemispherical prosthetic acetabulum, a hemispherical cap insertable into a cavity inside said acetabulum and a stabilizing ring positioned outside said acetabulum and connectable thereto, said acetabulum adapted to fit in said iliac fossa through said stabilizing ring which includes a junction and is provided on its external circumference with hooks, said cap being provided with anchorage means for fitting by pressure on said femoral head, an outside surface of said cap having round projections to reduce the friction with the inner surface of said cavity inside said acetabulum, said cap being further connected with holding means adapted to hold it stably on the femoral head.

2. The prosthesis according to claim 1, wherein the top of said prosthetic acetabuhm has a control opening or hole for technical and biological application purposes.

3. The prosthesis according to claim 1, wherin said anchorage means of said cap with said femoral head consists of a notching realized along the whole rim of said cap.

4. The prosthesis according to claim 3, wherein on the top of said cap there is a seat with a central opening or hole.

5. The prosthesis according to claim 1, wherein inside said cap there is an alveolate structure with holes which communicate with the outside surface of said cap.

6. The prosthesis according to claim 1, wherein said round projections are radial grains, segments having a hemispherical or a different shape or sliding blocks.

7. The prosthesis according to claim 1, wherein said stabilizing ring includes cavities which include an inclined plane placed on the inner surface of said ring which allow the fitting and the passage of radial projections on the external surface of said acetabulum which, rotating, connect said acetabulum to said stabilizing ring.

8. The prosthesis according to claim 1, wherein said stabilizing ring is made of a "shape-memorizing" material.

9. The prosthesis according to claim 1, wherein said holding means adapted to hold said cap on said femoral head include a higher blind compensator which is threaded inside and is provided with a head, a stirrup, a lower passing compensator and a tie.

10. The prosthesis according to claim 9, wherein said tie is provided with a head on a first end and with a threading on the opposite end.

11. A prosthesis according to claim 9, wherein said tie is inserted in said lower passing compensator, then in said stirrup and sized to penetrate from the top of the femoral diaphysis under the great trochanter, it passes obliquely through the whole higher femoral epiphysis and through the center of the femoral neck and head in order to be screwed to said higher blind compensator, whose head placed in said seat of said cap constrains all.

12. The prosthesis according to claim 9, wherein said stirrup has a structural C-shape reproducing the shape of the external and lateral cortex of the femur under the great trochanter and wherein said stirrup is provided with a niche with a central and oblong opening apt to house said lower passing compensator, having a flat side and a convex side, and said head of said tie.

13. The prosthesis according to claim 12, wherein said convex side of said lower passing compensator and said central oblong opening of said niche of said stirrup allow said tie to rotate together with said lower passing compensator with reference to said stirrup to adapt said prosthesis to the specific geometrical characteristics of the patient's femur.

14. The prosthesis according to claim 1, wherein all components of said prosthesis are made of a defined "inert", highly biocompatible material.

15. The prosthesis according to claim 1, wherein said round projections are circular rises.

* * * * *